(12) United States Patent
Sidawi

(10) Patent No.: US 10,562,670 B1
(45) Date of Patent: Feb. 18, 2020

(54) FRAGRANCE DISPENSER REFILL WITH LOCKING BOTTLE

(71) Applicant: Silver Coast, Inc., Milton (CA)

(72) Inventor: Rami Sidawi, Milton (CA)

(*) Notice: Subject to any disclaimer, the term of this patent is extended or adjusted under 35 U.S.C. 154(b) by 376 days.

(21) Appl. No.: 15/299,429

(22) Filed: Oct. 20, 2016

Related U.S. Application Data

(60) Provisional application No. 62/244,182, filed on Oct. 20, 2015.

(51) Int. Cl.
| | | |
|---|---|---|
| *B65D 25/34* | (2006.01) | |
| *B65D 23/08* | (2006.01) | |
| *A61L 9/04* | (2006.01) | |
| *B65D 75/00* | (2006.01) | |
| *B65D 1/02* | (2006.01) | |

(52) U.S. Cl.
CPC ............... *B65D 23/08* (2013.01); *A61L 9/04* (2013.01); *B65D 1/0223* (2013.01); *B65D 75/002* (2013.01); *A61L 2209/133* (2013.01); *B65D 2501/0009* (2013.01)

(58) Field of Classification Search
CPC ...... B65D 23/08; B65D 1/0223; B65D 25/34; B65D 23/0857; B65D 23/0885; A61L 9/04; A61L 2209/133

USPC ........................................................ 215/12.1
See application file for complete search history.

(56) References Cited

U.S. PATENT DOCUMENTS

| | | | | |
|---|---|---|---|---|
| 2005/0023371 A1* | 2/2005 | Joshi | ....................... | A61L 9/037 239/60 |
| 2012/0125943 A1* | 5/2012 | Lee | ..................... | A47J 41/0061 220/739 |
| 2014/0103136 A1 | 4/2014 | Sidawi | | |

* cited by examiner

*Primary Examiner* — Stephen J Castellano
(74) *Attorney, Agent, or Firm* — Angus C. Fox, III; Brick Power

(57) ABSTRACT

A refill for a commercial fragrance dispenser includes a bottle that is capable of irremovably locking into place within a respective fragrance distribution elements, or cage. Such a configuration may prevent inadvertent spilling of fragrance from the bottle. A lock preventer may enable the bottle to be stored within the cage while preventing full insertion of the bottle of the refill into the receptacle of the cage of the refill until assembly of the bottle with the cage and of the cage with the body of a commercial fragrance dispenser are desired. Methods for refilling fragrance dispensers, in which the bottle of a refill is locked within a cage of the refill and coupled to the cage or dispenser, are also disclosed.

10 Claims, 5 Drawing Sheets

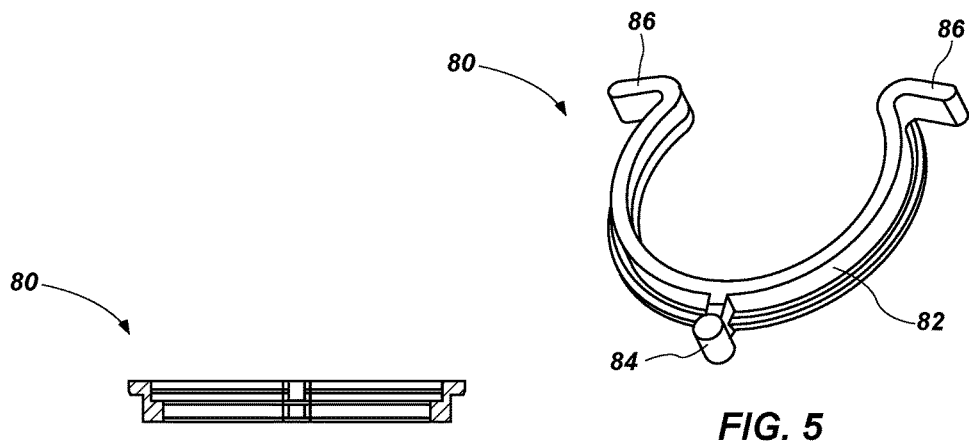
FIG. 5
FIG. 5A
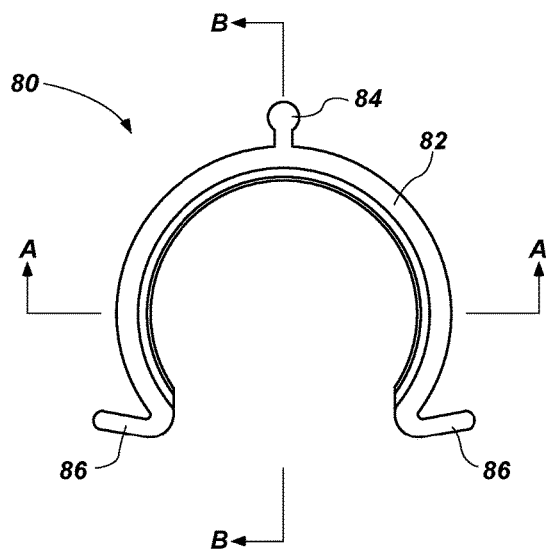
FIG. 5C
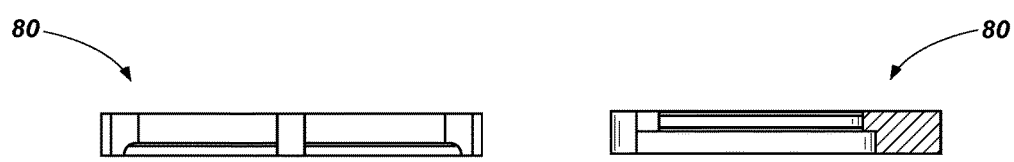
FIG. 5D
FIG. 5B

FRAGRANCE DISPENSER REFILL WITH LOCKING BOTTLE

CROSS-REFERENCE TO RELATED APPLICATION

A claim for priority is hereby made, pursuant to 35 U.S.C. § 119(e), to the Oct. 20, 2015 filing date of U.S. Provisional Patent Application No. 62/244,182, titled FRAGRANCE DISPENSER REFILL WITH LOCKING BOTTLE ("the '182 Provisional Application"). The entire disclosure of the '182 Provisional Application is hereby incorporated herein.

TECHNICAL FIELD

This disclosure relates generally to refills for commercial fragrance dispensers and, more specifically, to refills with bottles that are configured to irremovably lock into place within their respective fragrance distribution elements, or cages. Such a configuration may prevent inadvertent spilling of fragrance from the bottle. Methods for refilling fragrance dispensers, in which the bottle of a refill is locked within a cage of the refill and coupled to the cage, are also disclosed.

SUMMARY

A refill for a fragrance dispenser of the type commonly used in high-traffic restrooms (e.g., public restrooms, restrooms in commercial buildings, etc.) includes a bottle and a fragrance distribution element, which is also referred to herein as a "cage." The refill is configured in such a way that the bottle locks into place within a receptacle of the cage as the bottle is fully inserted into the receptacle and/or as the bottle and the cage are coupled to one another.

In some embodiments, the refill includes a locking element. The locking element may be configured to engage at least one locking feature of the bottle of the refill when the bottle is completely, or fully, inserted into the receptacle of the cage of the refill. The locking element may be configured to prevent removal of the bottle from the receptacle.

In some embodiments, the locking element may be associated with a mouth of the cage. More specifically, the locking element may be located on the mouth of the cage or adjacent to the mouth of the cage. Even more specifically, the locking element may comprise an annular structure with an opening. A plurality of locking tabs that extend at least partially toward a center of the receptacle may be positioned around an inner periphery of the opening. Each locking tab may be configured to flex toward an inner surface of the receptacle as the bottle is introduced into the receptacle and as at least one locking feature—a locking protrusion—on the bottle is forced past the locking tabs. As the at least one locking protrusion on the bottle moves beyond the locking tabs, each locking tab that was flexed may resiliently return to its original position, in which the locking tabs of the locking element and the at least one locking protrusion on the bottle prevent removal of the bottle from the receptacle of the cage.

A refill according to this disclosure may also include a lock preventer. The lock preventer may be configured to engage or to be engaged by a lock prevention feature of the bottle. The lock preventer may be configured to prevent full insertion of the bottle of the refill into the receptacle of the cage of the refill. Thus, a configuration of the lock preventer, when assembled with the bottle, may prevent coupling of the bottle to the cage.

In some embodiments, when the lock preventer is deployed (e.g., assembled with a lock prevention feature of the bottle, etc.), it may protrude beyond an outer surface of the bottle in a manner that inhibits insertion of the lock preventer and the portion of the bottle with which the lock preventer is associated from being inserted into the receptacle of the cage.

In another aspect, methods for refilling fragrance dispensers are disclosed. Such a method may include opening a package that contains a refill, including a cage and a bottle that have not been completely assembled with one another. A lock preventer may be removed from the bottle to enable the bottle to be completely inserted into a receptacle of the cage and to enable coupling of the bottle to a base of the cage in a manner that enables fragrance to be dispersed into an environment where the refill and/or the fragrance dispenser are located (e.g., a bathroom, etc.). As the bottle is completely inserted into the receptacle of the cage and/or as the bottle is coupled with the base of the cage, the bottle may be locked within the receptacle in a manner that prevents removal of the bottle from the receptacle. Locking of the bottle within the receptacle may also prevent uncoupling of the bottle from the base of the cage and, thus, reduce the likelihood of spilling any fragrance from the bottle. With the bottle locked into place within the receptacle of the cage and the bottle coupled with the base of the cage, the cage-bottle assembly may be introduced into a fragrance dispenser.

Other aspects, as well as features and advantages of various aspects, of the disclosed subject matter will become apparent to those of ordinary skill in the art through consideration of the ensuing description, the accompanying drawings and the appended claims.

BRIEF DESCRIPTION OF THE DRAWINGS

In the drawings:

FIG. 2 is a perspective view of the refill in the partially assembled relationship illustrated by FIG. 1, without the package, and showing a locking element at a mouth of the;

FIGS. 5 and 5A-5D provide various views of an embodiment of a lock preventer that may be used with the embodiment of bottle shown in FIGS. 4A-4C.

DETAILED DESCRIPTION

Figure 1:
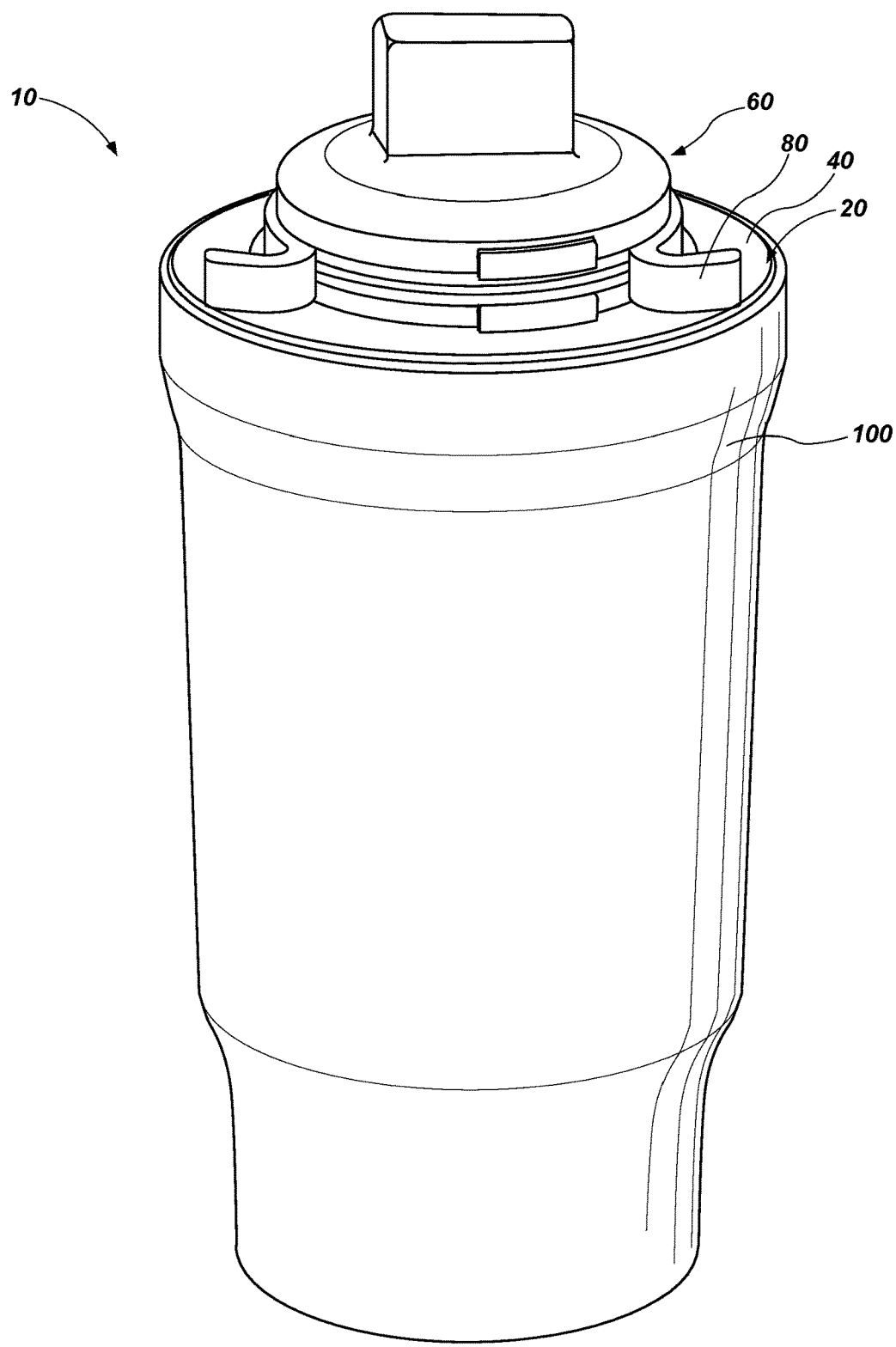
FIG. 1 is a perspective view of an embodiment of a packaged refill for a fragrance dispenser, the packaged refill including a cage, a bottle disposed partially within a receptacle of the cage, a locking preventer preventing the bottle from being completely disposed within the receptacle of the cage and a package (e.g., a shrink wrap wrapper, etc.) holding the cage, the bottle and the locking preventer in this partially assembled arrangement for transportation and/or storage.

FIG. 1 illustrates an embodiment of a refill 10 for a fragrance dispenser of the type often found in high-traffic restrooms (i.e., lavatories, water closets, etc.). More specifically, FIG. 1 shows the refill 10 in a packaged, partially assembled arrangement, which is the arrangement the refill 10 is in when it is being stored and transported. As illustrated, the refill 10 includes a fragrance distribution element, which is also referred to herein as a "cage" 20, as well as a bottle 60 and a package 100.

The cage 20 and the bottle 60 may have any suitable configurations, such as the general configurations disclosed by U.S. Patent Application Publication 2014/0103136 of Sidawi ("Sidawi"), the entire disclosure of which is hereby incorporated herein. In addition to the configurations and features disclosed by Sidawi, the cage 20 and the bottle 60 may be configured in a way that enables the bottle 60 to be locked into place within a receptacle (not shown) of the cage 20, as will be described in further detail hereinafter.

The package 100 may have any suitable configuration that will hold the bottle 60 in place within the receptacle of the cage 20 without being functionally coupled to the cage 20. In the illustrated embodiment, the package 100 comprises a shrink wrap material positioned around the cage 20 and over an end of the bottle 60 protruding from the cage. Of course, other embodiments of packages may also be used to hold a cage 20 and a bottle 60 together during storage or transportation prior to operatively coupling the bottle to the cage 20.

Figure 2:
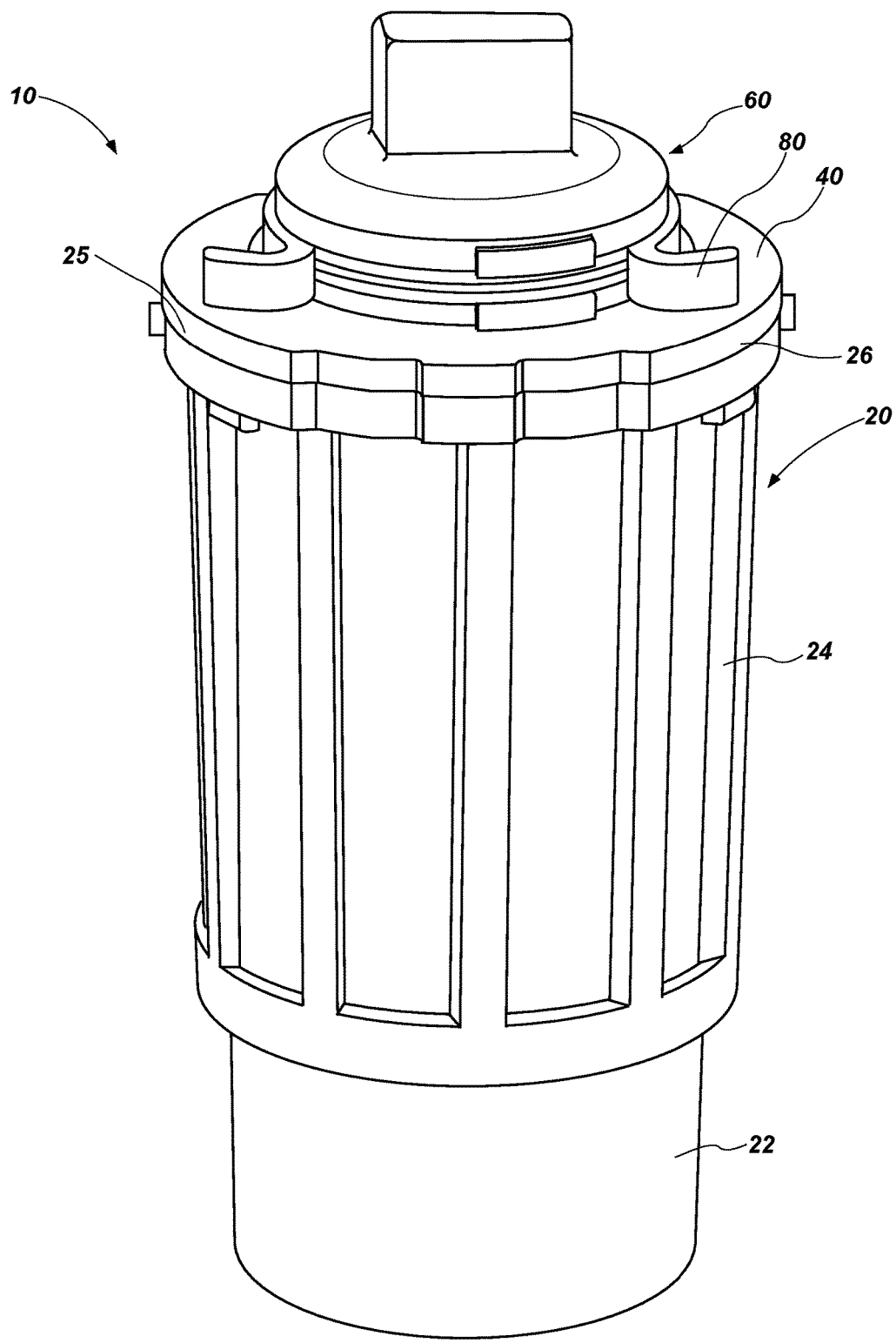

In the embodiment of refill 10 illustrated by FIG. 2, which is the same as the embodiment shown in FIG. 1, but with the package 100 (FIG. 1) removed, it can be seen that the cage 20 includes a base 22 at one end, a wall 24 extending from the base 22 and a mouth 26 at an opposite end of the cage 20. The mouth 26 opens to the receptacle (not shown) of the cage 20, within which the bottle 60 may be placed.

A locking element 40 is located at or adjacent to the mouth 26 of the cage 20. In the embodiment depicted by FIG. 2, the locking element 40 is secured to the end of the cage 20 that defines the mouth.

Figure 3A:
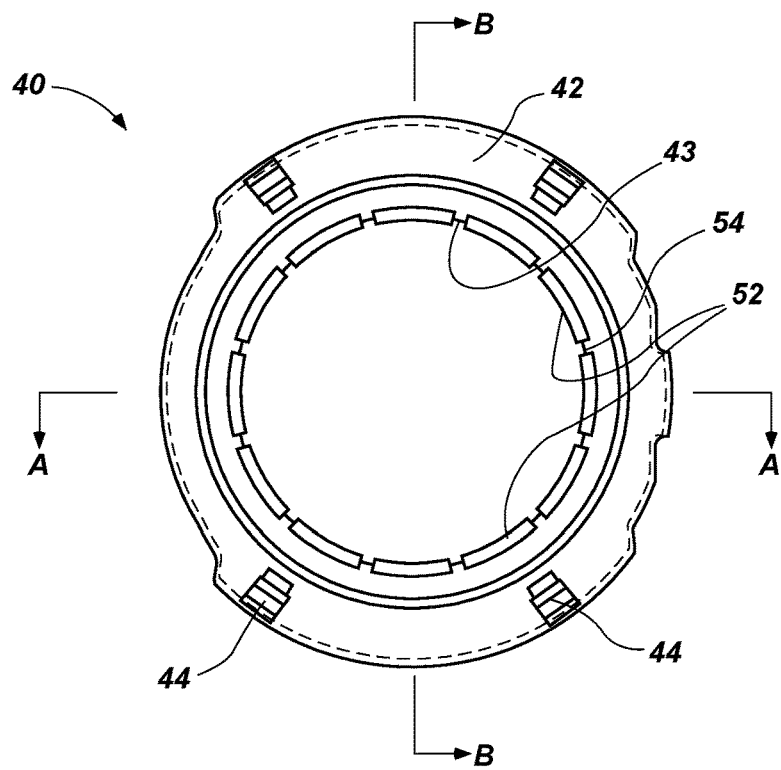
FIGS. 3A-3C provide bottom and side views of the embodiment of locking element shown in FIG. 2.
Figure 3B:
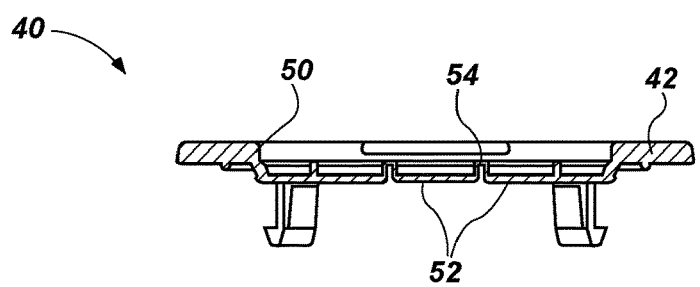
Figure 3C:
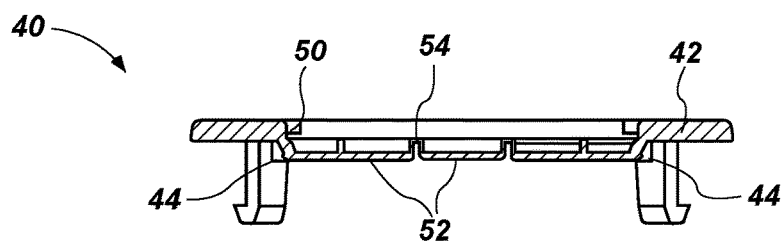

With reference turned to FIGS. 3A-3C, a specific embodiment of locking element 40 of a refill 10 for a fragrance dispenser is illustrated and described. The locking element 40 includes a peripheral element 42 that is configured to be secured to the end 25 (FIG. 2) of the cage 20 (FIG. 2) that defines the mouth 26 (FIG. 2) of the cage 20. In this regard, the locking element 40 may include a plurality of coupling tabs 44 that protrude from a surface of the outer periphery 42 that is to be disposed against the end 25 of the cage 20. Each coupling tab 25 may be configured to be received by and to engage a corresponding receptacle formed in the end 25 of the cage 20 in a manner that will secure the locking element 40 to the end 25 of the cage 20.

In FIG. 3A, the peripheral element 42 of the locking element 40 is shown as having an annular configuration. Regardless of its configuration, the peripheral element 42 includes an inner periphery 43 that defines an opening 50 through the locking element 40. The opening 50 through the locking element 40 is configured to be aligned with an opening (not shown) defined by the mouth 26 (FIG. 2) of the cage 20 (FIG. 2) and to communicate with the mouth 26 of the cage 20.

With continued reference to FIG. 3A, and with added reference to FIGS. 3B and 3C, the locking element 40 may also include a plurality of locking tabs 52, which may be positioned around the inner periphery 43 of the peripheral element 42 of the locking element 40. Each locking tab 52 may have an unflexed orientation in which, when the locking element 40 is secured to the end 25 of the cage 20, the locking tab 52 extends at least partially toward a center of the receptacle (not shown) of the cage 20. Each locking tab may be configured to flex toward the wall 24 of the cage 20 to a flexed orientation and to resiliently return to the unflexed orientation. As illustrated, locking tabs 52 may be positioned adjacent to one another. The distance, or gap 54, between adjacent locking tabs 52 and/or between a locking tab 52 and another peripherally (or circumferentially) adjacent feature of the locking element 40 may be small enough that corresponding locking features on the bottle 60 cannot pass between the locking tab 52 and the peripherally adjacent feature without contacting the locking tab 52 or the peripherally adjacent feature.

Figure 4A:
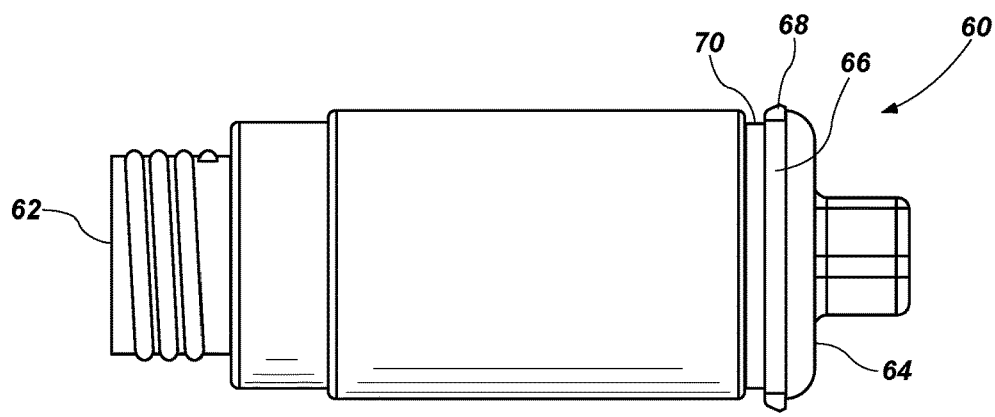
FIGS. 4A-4C provide side views and a top view of the embodiment of bottle of the refill of FIGS. 1 and 2.
Figure 4B:
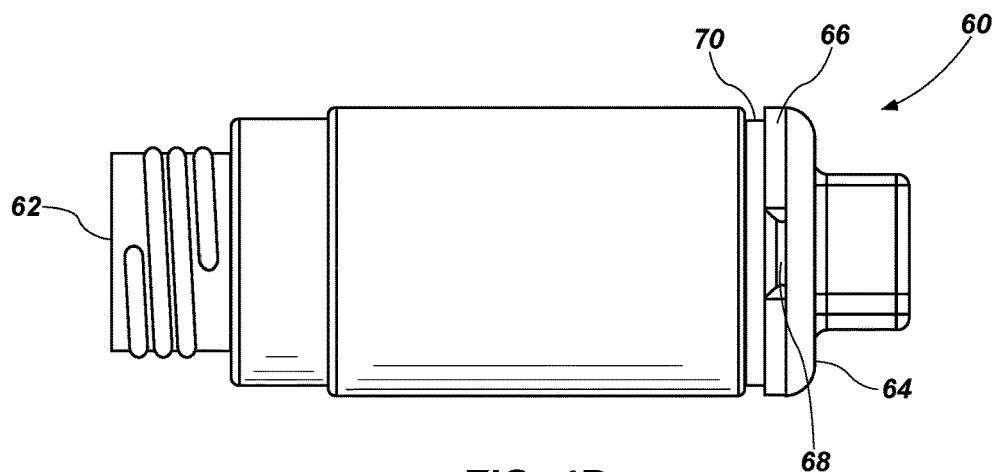
Figure 4C:
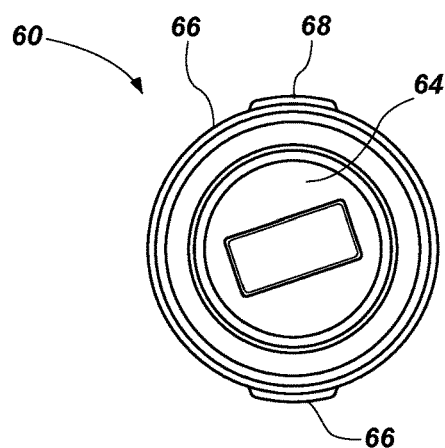

Referring now to FIGS. 4A-4C, a specific embodiment of the bottle 60 of a refill 10 according to this disclosure is depicted. The bottle 60, which is configured to be introduced through the opening 50 (FIGS. 3A-3C) through the locking element 40 (FIGS. 3A-3C), into the opening (not shown) of the mouth 26 (FIG. 2) of the cage 20 (FIG. 2) and into the receptacle (not shown) of the cage 20, includes a first end 62 and a second end 64. The first end 62, which includes a mouth (not shown) of the bottle 60, is configured to be positioned within the receptacle of the cage 20 and to functional couple with an interior portion (not shown) of the base 22 (FIG. 2) of the cage 20 in a manner that enables fragrance to be withdrawn from the bottle 60 and dispersed (e.g., in the manner disclosed by Sidawi, etc.) into an environment in which the refill 10 of which the bottle 60 and the cage 20 are a part has been placed, or in which a fragrance dispenser with which the refill 10 is assembled has been placed. An individual may grasp a feature (e.g., a handle, etc.) on the second end 64 of the bottle 60 as he or she positions the bottle 60 within the receptacle of the cage 20 and couples the first end 62 of the bottle 60 to the interior portion of the base 22 of the cage 20.

At or adjacent to its second end 64, at least one locking feature 68 may protrude from an outer surface 66 of the bottle 60. In the illustrated embodiment, a pair of diametrically opposed locking features 68 protrude from the bottle. Such a locking feature 63 may also be referred to herein as a "locking protrusion." Each locking feature 68 may comprise an integral feature of the bottle 60. Alternatively, one or more locking features 68 may be assembled with a bottle 60. In some embodiments, a distance across each locking feature 68, or its width, may be about the same as or less than a distance across, or width of, each locking tab 54 of the locking element 40 of the refill 10. In other embodiments, the distance across a locking feature 68 may exceed the distance across a locking tab 54 of the locking element 40.

In the illustrated embodiment, each locking feature 68 may be configured to urge at least one locking tab 54 (FIGS. 3A-3C) of the locking element 40 (FIGS. 3A-3C) from its unflexed orientation to its flexed orientation as the bottle 60 is inserted through the opening 50 (FIGS. 3A-3C) of the locking element 40 and into the receptacle (not shown) of the cage 20 (FIG. 2). In addition, each locking feature 68 may be configured to enable the at each locking tab 54 that has been flexed to return to its unflexed orientation as the bottle 60 is fully inserted into the receptacle of the cage 20. Together, the locking tabs 54 of the locking element 40 and the locking feature(s) 68 of the bottle 60 may be configured to prevent removal of the bottle 60 from the receptacle of the cage 20 when the locking feature(s) 68 is (are) located between the locking tabs 54 and the base 22 (FIG. 2) of the cage 20.

While FIGS. 4A-4C show an embodiment of the bottle 60 in which the locking features 68 are located adjacent to the second end 64 of the bottle 60, these and other embodiments of locking features 68 may be positioned at different locations along the length or height of the bottle 60.

With continued reference to FIGS. 4A-4C, a bottle 60 of a refill 10 according to this disclosure may include a lock prevention feature 70. The lock prevention feature 70 may be located at or adjacent to the second end 64 of the bottle 60. In the illustrated embodiment, the lock prevention feature 70 comprises a recess in the outer surface 66 of the bottle 60. The lock prevention feature 70 may comprise an elongated recess that extends at least partially around a periphery (e.g., circumference, etc.) of the bottle 60. In some embodiments, the lock prevention feature 70 may comprise a recess that extends completely around the periphery of the bottle 60 (e.g., a circumferential recess, etc.).

Looking now to FIGS. 5-5C, an embodiment of a lock preventer 80 of a refill 10 according to this disclosure is illustrated. In the illustrated embodiment, the lock preventer 80 may comprise a clip 82 that is configured engage (e.g., be received by, etc.) the lock prevention feature 70 (FIGS. 4A-4C) of the bottle 60 (FIGS. 4A-4C). In some embodiments, the clip 82 may be resilient. The clip 82 and/or other features of the lock preventer 82 may protrude beyond the outer surface 66 (FIGS. 4A-4C) of the bottle 60. A non-limiting example of a feature of a lock preventer 80 that may protrude outwardly from the clip 82 is a handle 84, which may facilitate assembly of the lock preventer 80 with the lock prevention feature 70 of the bottle 60 and removal of the lock preventer 80 from the lock prevention feature 70. As another example, tabs 86 may protrude outwardly from the ends of the clip 82.

When the lock preventer 80 is assembled with the lock prevention feature 70 (FIGS. 4A-4C) of the bottle 60 (FIGS. 4A-4C), the features of the lock preventer 80 that protrude beyond the outer surface 66 (FIGS. 4A-4C) of the bottle 60 may prevent the bottle 60 from being fully inserted into the receptacle (not shown) of the cage 20 (FIG. 2) of the refill 10 and to prevent the locking feature(s) 68 (FIGS. 4A-4C) of the bottle 60 from being positioned between the locking tabs (FIGS. 3A-3C) of the locking element 40 (FIGS. 3A-3C) and the base 22 (FIG. 2) of the cage 20.

Although the preceding disclosure provides many specifics, these should not be construed as limiting the scope of any of the ensuing claims. Other embodiments may be devised which do not depart from the scopes of the claims. Features from different embodiments may be employed in combination. The scope of each claim is, therefore, indicated and limited only by its plain language and the full scope of available legal equivalents to its elements.

What is claimed:

1. A refill for a fragrance dispenser, comprising:
a cage, the cage including a base and a wall, the base including a coupling element, the wall extending from the base, inner surfaces of the wall defining a receptacle of the cage, an upper edge of the wall defining a mouth of the cage;
a locking element on or adjacent to the mouth of the cage, the locking element including a plurality of locking tabs, each locking tab of the plurality of locking tabs having an unflexed orientation in which the locking tab extends at least partially toward a center of the receptacle of the cage, each locking tab being configured to flex toward the wall of the cage to a flexed orientation and to resiliently return to the unflexed orientation;
a bottle configured to be placed through the locking element and into the mouth and the receptacle of the cage, the bottle including a first end and a second end that are opposite from one another, a mouth at the first end and at least one locking protrusion at or adjacent to the second end, the mouth of the bottle configured to couple with the base of the cage when the bottle is fully inserted into the receptacle of the cage, the at least one locking protrusion configured to urge at least one locking tab of the locking element from its unflexed orientation to its flexed orientation as the bottle is inserted into the receptacle and to enable the at least one locking tab to return to its unflexed orientation as the bottle is fully inserted into the receptacle, the plurality of locking tabs of the locking element and the at least one locking protrusion of the bottle configured to prevent removal of the bottle from the receptacle when the at least one locking protrusion is located between the plurality of locking tabs and the base of the cage; and
a lock prevention feature at or adjacent to the second end of the bottle, said lock prevention feature including a lock preventer configured to be removably received by the lock prevention feature of the bottle, to prevent the bottle from being fully inserted into the receptacle of the cage and to prevent the at least one locking protrusion of the bottle from being positioned between the plurality of locking tabs of the locking element and the base of the cage.

2. The refill of claim 1, wherein the lock prevention feature of the bottle comprises a recess in the bottle.

3. The refill of claim 2, wherein the recess of the lock prevention feature of the bottle comprises an elongated recess extending at least partially around a periphery of the bottle.

4. The refill of claim 3, wherein the elongated recess extending at least partially around the periphery of the bottle comprises a circumferential recess.

5. The refill of claim 2, wherein the lock preventer comprises a clip configured to removably engage the recess in the bottle.

6. The refill of claim 5, wherein the clip is configured to resiliently engage the recess in the bottle.

7. The refill of claim 1, wherein the at least one locking protrusion of the bottle protrudes from an outer surface of the bottle.

8. The refill of claim 7, wherein a gap between every adjacent pair of locking tabs of the plurality of locking tabs of the locking element has a width that is less than a width of the at least one locking protrusion of the bottle.

9. A refill for a fragrance dispenser, comprising:
a cage, the cage including a base and a wall, the base including a coupling element, the wall extending from the base, inner surfaces of the wall defining a receptacle of the cage, an upper edge of the wall defining a mouth of the cage;
a bottle configured to be placed into the mouth and the receptacle of the cage, the bottle including an outer surface, a first end and a second end that are opposite from one another, and a mouth at the first end and at least one locking feature at or adjacent to the second end, the mouth of the bottle configured to couple with the base of the cage when the bottle is fully inserted into the receptacle of the cage, the bottle having an elongated recess in its outer surface at or adjacent to the second end, the elongated recess extending at least partially around the bottle, and functioning as a lock prevention feature;
a locking element on or adjacent to the mouth of the cage, the locking element configured to engage the at least one locking feature of the bottle when the bottle is fully inserted into the receptacle of the cage and to prevent removal of the bottle from the receptacle; and
a lock preventer configured to be removably received by the lock prevention feature of the bottle, to prevent the bottle from being fully inserted into the receptacle of the cage and to prevent the at least one locking feature of the bottle from being positioned between the plurality of locking tabs of the locking element and the base of the cage.

10. The refill of claim 9, wherein the lock preventer comprises a clip configured to be received by the elongated recess of the lock prevention feature of the bottle and to at least partially surround the outer surface of the bottle and to protrude from a plurality of locations around the outer surface of the bottle.

\* \* \* \* \*